United States Patent [19]

Cheung et al.

[11] Patent Number: 5,489,565
[45] Date of Patent: Feb. 6, 1996

[54] HYDROGENATION PROCESS AND CATALYST THEREFOR

[75] Inventors: Tin-Tack P. Cheung; Marvin M. Johnson, both of Bartlesville, Okla.

[73] Assignee: Phillips Petroleum Company, Bartlesville, Okla.

[21] Appl. No.: 418,038

[22] Filed: Apr. 6, 1995

Related U.S. Application Data

[62] Division of Ser. No. 277,056, Jul. 19, 1994.

[51] Int. Cl.[6] ..................................................... B01J 23/00
[52] U.S. Cl. .......................... 502/325; 502/330; 502/347; 585/259
[58] Field of Search .................................. 502/325, 330, 502/347

[56] References Cited

U.S. PATENT DOCUMENTS

| | | | |
|---|---|---|---|
| 3,932,548 | 1/1976 | Rausch | 585/434 |
| 4,068,477 | 11/1977 | Berribi | 585/274 |
| 4,409,410 | 10/1983 | Cosyns et al. | 585/259 |
| 5,032,565 | 7/1991 | Berribi | 502/231 |
| 5,059,731 | 10/1991 | Berribi | 585/259 |
| 5,208,405 | 5/1993 | Cheung et al. | 585/274 |

OTHER PUBLICATIONS

Yeung H. Park and Geoffrey L. Price, "Promotional Effects of Potassium on Pd/Al$_2$O$_3$ Selective Hydrogenation Catalysts", Ind. Eng. Chem. Res. 1992, 31, pp. 469–474.

*Primary Examiner*—Ponnathapura Achutamurthy
*Attorney, Agent, or Firm*—K. K. Brandes

[57] ABSTRACT

A supported catalyst composition, which is effective as a diolefin hydrogenation catalyst, comprises palladium, silver and alkali metal fluoride. This catalyst composition is employed in the selective hydrogenation of $C_4$–$C_{10}$ diolefins (preferably 1,3-butadiene) with hydrogen gas to the corresponding monoolefins.

12 Claims, No Drawings

HYDROGENATION PROCESS AND CATALYST THEREFOR

This is a division of pending application Ser. No. 08/277,056, filed Jul. 19, 1994.

BACKGROUND OF THE INVENTION

In one aspect, this invention relates to a supported noble metal catalyst composition. In another aspect, this invention relates to a selective diolefin (diene) hydrogenation process employing a supported noble metal catalyst composition. In still a further aspect, this invention relates to a process for the selective hydrogenation of 1,3-butadiene to butenes employing a supported noble metal catalyst composition.

Catalysts comprising palladium, silver and a support material are known diene hydrogenation catalysts. For instance, U.S. Pat. No. 4,409,410 discloses the use of a Pd/Ag/Al$_2$O$_3$ catalyst for the selective hydrogenation of butadiene to butenes. Even though supported Pd/Ag catalysts are effective hydrogenation catalysts, there is an ever present need for further improvements (e.g., for enhanced selectivity to monoolefins and/or increased catalyst life.). The present invention is directed to an improved, modified catalyst compositions and its use in processes for the selective hydrogenation of diolefins to monoolefins, preferably of 1,3-butadiene to butenes.

SUMMARY OF THE INVENTION

It is an object of this invention to provide an improved palladium/silver-containing catalyst composition. It is another object of this invention to employ this improved catalyst composition in the selective hydrogenation of diolefins to monoolefins. It is a further object of this invention to employ this improved catalyst composition in the selective hydrogenation of 1.3-butadiene to butenes. Other objects and advantages will be apparent from the detailed description and the appended claims.

In accordance with this invention, a catalyst composition is provided which comprises (a) at least one palladium-containing material selected from the group consisting of palladium metal and palladium compounds, (b) at least one silver-containing material selected from the group consisting of silver metal and silver compounds. (c) at least one alkali metal fluoride, and (d) at least one inorganic support material. In a preferred embodiment, the inorganic support is alumina and the alkali metal fluoride is potassium fluoride.

Also in accordance with this invention, an improved process for selectively hydrogenating C$_4$–C$_{10}$ diolefins with hydrogen gas to the corresponding C$_4$–C$_{10}$ monoolefins is carried out with the catalyst composition of this invention. In a preferred embodiment, 1,3-butadiene (more preferably present in small amounts in butene-containing gas streams) is selectively hydrogenated with hydrogen gas to at least one butene in the presence of the catalyst composition of this invention.

DETAILED DESCRIPTION OF THE INVENTION

The composition of matter of this invention comprises (preferably consists essentially of) (a) palladium metal and/or at least one palladium compound (preferably palladium oxide), (b) silver metal and/or at least one silver compound (preferably silver oxide), (c) at least one alkali metal fluoride (preferably potassium fluoride), and (d) an inorganic support material selected from the group consisting of alumina, silica, titania, zirconia, aluminosilicates, zinc aluminate, zinc titanate, and mixtures of two or more than two of these compounds, preferably alumina, more preferably alpha-alumina. Generally, the catalyst composition comprises 0.01–2 (preferably about 0.05–0.6) weight-% Pd, about 0.02–10 (preferably about 0.1–5) weight-% Ag, and about 0.05–10 weight-% (preferably about 0.2–5) weight-% alkali metal (preferably K). The catalyst particles can have any suitable shape (spherical, cylindrical, trilobal and the like), and are preferably either spheres or cyclindrical extrudates. The catalyst particles can have any suitable particle size, and generally have a size of about 1–10 nun (preferably about 2–6 mm). The catalyst particles can have any suitable surface area (measured by the BET method by Bruhauer. Emmett and Teller employing N$_2$), and generally have a surface area of about 1–200 (preferably about 10–100) m$^2$/g.

The catalyst particles can be prepared by any suitable means. The promoter components (a), (b) and (c) can be deposited onto and/or incorporated into the inorganic support material by any suitable means and in any suitable order. For instance, the alkali metal fluoride can be incorporated into the support material, followed by impregnation of the fluoride-containing support material with Pd and Ag compounds (such as H$_2$PdCl$_4$ and AgNO$_3$), sequentially in any order or simultaneously, followed by drying and calcining of the thus-impregnated composition. Or a supported palladium catalyst composition (preferably a Pd/Al$_2$O$_3$ composition which is commercially available, e.g., from Mallinckrodt Specialty Chemicals Company, Erie, Pa.) can be impregnated with a silver compound and an alkali metal fluoride, either sequentially in any order or simultaneously, followed by drying and calcining of the thus-impregnated composition. Mainly for economic reasons, it is presently not preferred to prepare the catalyst composition by a method which includes an additional low-temperature wet-reduction step (i.e., treatment with a reducing agent dissolved or dispersed in a liquid medium, at a temperature of up to about 60° C.). Preferably, the catalyst composition of this invention is prepared by incorporating alkali metal fluoride into a supported Pd/Ag-containing base catalyst, as described below.

The preferred starting material (also referred to as "base catalyst") which is to be improved in accordance with this invention by incorporation of alkali metal fluoride therein, can be any supported palladium- and silver-containing composition. The base catalyst composition can be a fresh butadiene hydrogenation catalyst; or it can be a used and thereafter oxidatively regenerated butadiene hydrogenation catalyst composition; or it can be a butadiene hydrogenation catalyst composition which has previously been treated with a wet-reducing agent (such as dissolved formaldehyde, formic acid, ascorbic acid, dextrose, hydrazine, alkali metal borohydride and the like), at a low temperature of up to about 60° C. (preferably about 10°–50° C.), as has been described in Example I. Broadly, the base catalyst can contain about 0.01–2 (preferably about 0.05–0.6) weight-% Pd, about 0.02–10 (preferably about 0.1–5) weight-% Ag and a suitable solid inorganic support material, preferably alumina (more preferably alpha-alumina). Preferably, the Ag:Pd weight ratio in the catalyst is about 1:1 to about 20:1, more preferably about 2:1 to about 10.1. The supported Pd/Ag base catalyst particles can have any suitable shape, and preferably are spherical pellets or cylindrical extrudates. The size of these supported Pd/Ag base catalyst particles generally is about 1–10 mm, preferably about 2–6 mm, and its surface generally is about 1–200 m$^2$/g.

In the preferred method of preparing the catalyst composition of this invention, a Pd/Ag-containing base catalyst (described above) is contacted with a solution (preferably aqueous) of at least one alkali metal fluoride (preferably KF) at such conditions as to incorporate about 0.05–10 (preferably about 0.2–5) weight-% of alkali metal (preferably potassium) into the catalyst composition. Generally, the concentration of the alkali metal fluoride in the contacting (impregnating) solution is about 0.1–10 mol/l (preferably about 0.2–3 mol/l). The preferred contacting method is "incipient wetness impregnation", i.e. essentially completely filling the pores of the base catalyst with the alkali metal fluoride solution. Generally, the weight ratio of the solution to the solid base catalyst composition is in the range of about 0.2:1 to about 2:1, preferably about 0.4:1 to about 1:1 (depending on the fluoride concentration of the impregnating solution and the desired alkali metal fluoride level in the catalyst composition of this invention). Thereafter, the catalyst composition is substantially dried (preferably at about 50°–150° C. for about 0.5–20 hours) and calcined (preferably in an oxidizing gas atmosphere, more preferably air) at a temperature of about 300°–600° C. (preferably about 300°–500° C.) for about 0.2–20 hours (preferably about 1–8 hours).

The catalyst composition of this invention is preferably employed in the selective hydrogenation of diolefins containing 4–10 carbon atoms per molecule to the corresponding monoolefins containing 4–10 carbon atoms per molecule, particularly of 1,3-butadiene to primarily butenes (butene-1, butene-2). The calcined catalyst composition of this invention can be employed directly in this selective hydrogenation process. However, it is preferred to first treat the catalyst with a reducing gas such as hydrogen, because the optimum operation of the selective hydrogenation does not begin until there has been a substantial reduction of the catalytic metals. Typically, the reduction is carried out at a temperature in the range of about 10° C. to about 100° C. for at least 10 minutes (preferably about 1–10 hours).

Non-limiting examples of suitable diolefins containing 4–10 carbon atoms per molecule which can be hydrogenated in the process of this invention include 1,2-butadiene, 1,3-butadiene, isoprene, 1,2-pentadiene, 1,3-pentadiene, 1,2-hexadiene, 1,3-hexadiene, 1,4-hexadiene, 1,5-hexadiene, 2-methyl-1,2-pentadiene, 2,3-dimethyl-1,3-butadiene, heptadienes, octadienes, nonadienes decadienes, cyclopentadiene, cyclohexadiene, methylcyclopentadienes, cycloheptadienes, methylcyclohexadienes dimethylcyclopentadienes, ethylcyclopentadienes, octadienes, methylheptadienes, dimethylhexadienes. ethylhexadienes, trimethylpentadienes, methyloctadienes, dimethylheptadienes, ethylheptadienes, trimethylheptadienes, and mixtures of one or two of these diolefins. Presently preferred are diolefins containing 4–6 carbon atoms per molecule.

The diolefin-containing feed for the hydrogenation process of this invention can also contain other hydrocarbons, in particular, monoolefins. Non-limiting examples of such monoolefins which can be present in the feed at a level of at least 30 volume-% include ethylene. propylene, 1-butene, 2-butene, isobutylene, 1-pentene, 2-pentene, methyl-1-butenes (such as 2-methyl-l-butene), methyl-2-butenes (such as 2-methyl- 2-butene), 1-hexene, 2-hexene, 3-hexene, methyl-1-pentenes, 2,3-dimethyl-1-butene. 1-heptene, 2-heptene, 3-heptene, methyl-1-hexenes, methyl-2-hexenes, methyl-3-hexenes. dimethylpentenes, ethylpentenes, octenes, methylheptenes, dimethylhexenes, ethylhexenes, nonenes, methyloctenes, dimethylheptenes, ethylheptenes, trimethylhexenes, cyclopentene, cyclohexene, methylcyclopentenes, cycloheptene, methylcyclohexenes, dimethylcyclopentes, ethylcyclopentenes, cyclooctenes, methylcycloheptenes, dimethylcyclohexenes, ethylcyclohenenes, trimethylcyclohexenes, methylcyclooctenes, dimethylcyclooctenes, ethylcylcooctenes, and mixtures of two or more than two of these monolefins. Presently preferred are monolefins containing 4–6 carbon atoms per molecule.

The fluid feed (which may be liquid or gaseous at the hydrogenating conditions of this process) generally contains about 0.01–70 mole-% of at least one diolefin, preferably about 0.01 to about 10 mole-% of at least one diolefin. Generally, the fluid feed comprises at least one diolefin and additionally at least one monoolefin, preferably about 30–99.9 mole-% of at least one monoolefin. However, it is within the scope of this invention to employ feeds which contain more than about 70 mole-% of at least one diolefin, or even to employ feeds which consist essentially of at least one diolefin. Also, the feed can contain small amounts (generally less than about 0.01 mole-%) of sulfur compounds (such as $H_2S$, mercaptans, organic sulfides) and/or carbon monoxide (also generally less than about 0.01 mole-%) as impurities.

The selective hydrogenation process of this invention is generally carried out by contacting a feed stream containing at least one diolefin and molecular hydrogen with the catalyst (generally contained in a fixed bed). Generally, about 1–10 moles of hydrogen are employed for each mole of diolefin. The temperature necessary for the selective hydrogenation process of this invention depends largely upon the activity of the catalyst and the desired extent of diolefin hydrogenation. Generally, temperatures in the range of about 35° C. to about 200° C. are used. A suitable reaction pressure generally is in the range of about 20 to 2,000 pounds per square inch gauge (psig). The liquid hourly space velocity (LHSV) of the hydrocarbon feed can vary over a wide range. Typically, the space velocity of the feed will be in the range of about 3 to about 100 liters of hydrocarbon feed per liter of catalyst per hour, more preferably about 20 to about 80 liter/liter/hour. The hydrogenation process conditions should be such as to avoid significant hydrogenation of monoolefins (formed by hydrogenation of diolefins and/or being initially present in the feed) to paraffins.

In the preferred embodiment of the selective hydrogenation process of this invention, a hydrocarbon feed stream containing 1,3-butadiene and molecular hydrogen are contacted with the catalyst (generally contained in a fixed bed). Frequently, the hydrocarbon feed contains butenes as the primary components (comprising in excess of about 50 weight-%) and 1,3-butadiene as a minor component (present at a level of about 0.01 to about 10 weight-% butadiene). Preferably, this hydrogenation process employs about 1–2 moles $H_2$ per mole 1,3-butadiene. The reaction temperature necessary for the selective hydrogenation of 1,3-butadiene depends largely upon the activity of the catalyst and the desired extent of the 1,3-butadiene hydrogenation, and generally is in the range of about 35° C. to about 100° C. Any suitable reaction pressure can be employed. Generally, the total pressure is in the range of about 50 to 1,000 pounds per square inch gauge (psig). The liquid hourly space velocity (LHSV) of the hydrocarbon feed can also vary over a wide range. Typically, the space velocity will be in the range of about 3 to about 100 liters of hydrocarbon feed per liter of catalyst per hour, more preferably about 20 to about 80 liter/liter/hour. The hydrogenation process conditions should be such as to avoid significant hydrogenation of butenes to butane.

Regeneration of the catalyst composition of this invention (after it has been employed in a diolefin hydrogenation process) can be accomplished by heating the catalyst in an oxidizing gas, preferably air, at a temperature preferably not in excess of 700° C. (preferably at a temperature about 500°–650° C.) for a time period in the range of about 10 minutes to about 20 hours, to burn off any deposited or adsorbed organic matter (e.g., polymeric substances) or char. The regenerated catalyst can be reemployed in the selective hydrogenation process of this invention, generally after reduction with hydrogen, as described above.

The following examples are presented to further illustrate this invention and should not be construed as unduly limiting the scope of this invention.

EXAMPLE I

This example illustrates the preparation of various palladium-containing catalysts and their use in the selective hydrogenation of 1,3-butadiene to butenes.

Catalyst A1 (Control) was a Pd/Ag/Al$_2$O$_3$ catalyst, which had been provided by the Calsicat Catalyst Division of Mallinckrodt Specialty Chemicals Company, Erie, Pa. This catalyst had a BET/N$_2$ surface area of 35 m$^2$/g, a bulk density of 0.90 cc/g, and a particle size of 8–14 mesh. It contained 0.28 weight-% Pd and 1.85 weight-% Ag.

Catalyst A2 (Control) was prepared in a R&D laboratory of Phillips Petroleum Company, Bartlesville, Okla. by the following procedure: 20.03 grams of a Pd/Al$_2$O$_3$ catalyst (1/16 inch spheres containing about 0.3 weight-% Pd, marketed by Calsicat under the product designation of "E-143 SDU") were soaked for about 1 hour in 22 cc of an aqueous solution containing 1.03 gram of AgNO$_3$. Thereafter, excess solution was drained off, the soaked catalyst was dried at 190° F. for several hours, and the dried catalyst was calcined in air at 370° C. for 5 hours. This catalyst contained 0.35 weight-% Pd and 3.0 weight-% Ag.

Catalyst B (Invention) was prepared by soaking 80.17 grams of Calsicat E-143SDU (described above) with an aqueous solution of 4.08 grams of AgNO$_3$ in 72.3 grams of H$_2$O for about 1.5 hours. Excess liquid was drained from the Ag-impregnated catalyst, which was then dried at 180° F. for several days and calcined for 4.5 hours at 370° C. in air. Then 20.07 g of this Pd/Ag/Al$_2$O$_3$ catalyst material was soaked in 30 cc of a formaldehyde solution containing about 37 weight-% of formaldehyde, about 17 weight-% of methanol, and about 46 weight-% of water. About 0.5 g solid KOH was added to this mixture of catalyst and formaldehyde solution which was then stirred for 45 minutes. Thereafter, another aliquot of about 0.5 g solid KOH was added to this mixture. After soaking for 20 minutes, excess liquid was drained off, the catalyst was washed twice with methanol and then twice with distilled water (until the filtrate had a pH of about 7). This wet-reduced, catalyst, from which KOH had been removed by the above washing procedure, was dried overnight at 180° F. The dried catalyst was then impregnated with a solution of 0.441 g KF in 14.15 g H$_2$O. A large portion of water was removed from the mixture by heating at 180° F. (without prior draining of excess liquid). The obtained KF-impregnated Pd/Ag/Al$_2$O$_3$ catalyst was then dried overnight at 132° C. and calcined in air at 370° C. for 3 hours. Catalyst B contained about 0.28 weight-% Pd, about 2.6 weight-% Ag and about 1.3 weight-% K.

The above-described catalyst materials were tested in the selective hydrogenation of 1,3-butadiene by the following procedure. About 20 cc of each catalyst was placed into a stainless steel reactor tube having an inner diameter of 0.5 inch and a length of about 18 inches. Thermocouples were inserted into the top and bottom regions of the catalyst bed, which was heated by an external furnace. The hydrocarbon feed was liquid and contained about 5.1 mole-% 1,3-butadiene, about 16.4 mole-% cis-butene-2, about 27.4 mole-% trans-butene-2, about 44.1 mole-% butene-1, about 6.8 mole-% n-butane, and about 0.1 weight-% C$_6$+hydrocarbons. Hydrogen gas was fed with the liquid hydrocarbon feed so as to provide a H$_2$/butadiene mole ratio of about 1:1. The total pressure in the reactor was maintained at about 500 psig. The product gas was analyzed every 1–3 hours by means of a gas chromatograph. Pertinent process parameters and test results are summarized in Table I.

TABLE I

| Catalyst | Feed Rate of Liquid Hydrocarbons (cc/minute) | Feed Rate of Hydrogen Gas (cc/minute) | Average Reaction Temp. (°F.) | % Conversion of Butadiene | % Selectivity to Butenes | % Selectivity to Butane |
| --- | --- | --- | --- | --- | --- | --- |
| A1 (Control) | 9 | 104 | 106 | 73.7 | 64.1 | 35.8 |
| | 9 | 104 | 104 | 76.2 | 67.9 | 32.2 |
| | 9 | 104 | 104 | 78.4 | 70.9 | 29.1 |
| | 9 | 104 | 107 | 77.6 | 71.2 | 29 |
| | 9 | 104 | 108 | 78.6 | 74.6 | 25.4 |
| | 9 | 104 | 106 | 78.5 | 74.4 | 25.8 |
| | 9 | 104 | 108 | 78.9 | 75.8 | 24.3 |
| | 18 | 217 | 111 | 84.7 | 82.7 | 17.2 |
| | 18 | 217 | 108 | 83.9 | 84.9 | 15.5 |
| | 18 | 217 | 107 | 84.7 | 85.6 | 14.7 |
| | 18 | 217 | 106 | 84.7 | 84.9 | 15.4 |
| | 18 | 217 | 108 | 84.1 | 86 | 14.4 |
| A2 (Control) | 18 | 218 | 84 | 73.1 | 72.2 | 27.3 |
| | 18 | 218 | 97 | 85.1 | 83.7 | 15.4 |
| | 18 | 218 | 97 | 84.6 | 83.9 | 15.2 |
| | 18 | 218 | 104 | 84.8 | 83.4 | 15.7 |
| | 18 | 218 | 122 | 76.0 | 54.6 | 46.0 |
| | 18 | 218 | 123 | 75.4 | 60.8 | 39.8 |
| | 18 | 218 | 138 | 74.5 | 60.1 | 40.5 |
| | 18 | 218 | 141 | 74.0 | 70.4 | 30.1 |
| B (Invention) | 9 | 104 | 130 | 89.0 | 90.4 | 9.7 |
| | 9 | 104 | 122 | 90.4 | 91.7 | 8.4 |
| | 9 | 104 | 119 | 89.8 | 92.4 | 7.7 |

TABLE I-continued

| Catalyst | Feed Rate of Liquid Hydrocarbons (cc/minute) | Feed Rate of Hydrogen Gas (cc/minute) | Average Reaction Temp. (°F.) | % Conversion of Butadiene | % Selectivity to Butenes | % Selectivity to Butane |
|---|---|---|---|---|---|---|
| | 9 | 104 | 117 | 88.6 | 92.5 | 7.5 |
| | 9 | 104 | 118 | 89.9 | 91.6 | 8.6 |
| | 9 | 104 | 100 | 88.6 | 93.5 | 6.6 |
| | 9 | 104 | 98 | 87.0 | 94.0 | 6.0 |
| | 9 | 104 | 99 | 87.1 | 94.0 | 6.1 |
| | 9 | 104 | 98 | 87.0 | 94.3 | 5.7 |
| | 9 | 104 | 107 | 88.9 | 92.1 | 7.8 |
| | 9 | 104 | 106 | 86.8 | 92.7 | 7.4 |
| | 9 | 104 | 89 | 85.2 | 93.7 | 6.5 |
| | 9 | 104 | 90 | 83.6 | 94.2 | 5.8 |
| | 9 | 104 | 88 | 82.4 | 94.1 | 5.7 |
| | 9 | 104 | 94 | 88.1 | 95.1 | 5.1 |
| | 9 | 104 | 90 | 85.2 | 95.0 | 5.1 |
| | 9 | 104 | 88 | 84.0 | 95.5 | 4.6 |
| | 9 | 104 | 91 | 84.5 | 95.4 | 4.7 |
| | 9 | 104 | 98 | 84.4 | 95.4 | 4.6 |
| | 9 | 104 | 100 | 85.2 | 95.0 | 5.1 |
| | 9 | 104 | 100 | 85.4 | 95.1 | 5.0 |

Test data in Table I clearly show that the promotion of a Pd/Ag/Al$_2$O$_3$ catalyst with KF (resulting in Catalyst B) had a consistent beneficial effect on attained 1,3-butadiene conversion and selectivity to butenes (combined yields of butene-1 and butene-2 divided by butadiene conversion) versus control catalysts A1 and A2 (Pd/Ag/Al$_2$O$_3$ which had not been treated with KF). These test data also show that during the invention test, which lasted about 24 hours, Catalyst B exhibited good catalytic stability, as evidenced by a rather small drop in butadiene conversion and actually a slight increase in selectivity to the desired butenes. Thus, the butene yield (conversion times selectivity to butenes) remained approximately constant. Additional test data (not described herein) showed that the promotion of control catalyst A1 (Pd/Ag/Al$_2$O$_3$) with another potassium compound, KOH, resulted in a catalyst which exhibited unsatisfactory stability in a lengthy butadiene hydrogenation test, as evidenced by a significant decrease in catalytic activity and by process control (especially temperature control) problems.

EXAMPLE II

This example further illustrates the use of another KF-treated Pd/Ag/Al$_2$O$_3$ composition as a catalyst in the selective hydrogenation of 1,3-butadiene.

Catalyst C (Invention) was prepared by soaking 20.15 g Catalyst A1 (Pd/Ag/Al$_2$O$_3$, disclosed in Example I) with an aqueous solution of 1.448 g of KF in 14.3 g of distilled water. The obtained material was dried at 180° F. for several hours and calcined at 235° C. for 1.5 hour.

Catalyst C was tested as a catalyst in the selective hydrogenation of 1.3-butadiene to butenes, substantially in accordance with the procedure described in Example I, except that the liquid hydrocarbon feed contained 36.4 mole-% 1,3-butadiene, 13.1 mole-% trans-butene-2, 13.2 mole-% cis-butene-2, 30.2 mole-% butene-1, 7.2 mole-% n-butane, and 0.01 mole-% C$_6$+hydrocarbons. The total reactor pressure was about 500 psig. The feed rate of the liquid hydrocarbon feed ranged from about 1.5 cc/minute (during the first two days) to about 3.0 cc/minute (during the last day), and the feed rate of H$_2$ gas ranged from about 140 cc/minute (during the first day) to about 320 cc/minute (during the last day). A portion of the product was recycled to the reactor so as to attain a 3–6:1 recycle:feed volume ratio. The reaction temperature in the center of the catalyst bed was about 90°–100° F. during the entire test which lasted about 5 days. When the reaction had reached a steady state (after about 12 hours), the 1,3-butadiene content in the product ranged from about 6.0 mole-% to about 4.5 mole-% (during the last day), and the n-butane content in the product ranged from about 8.8 to about 8.2 mole-%. Thus, Catalyst C exhibited good catalytic activity and selectivity (to butenes). Furthermore, the fact that the catalyst performance did not deteriorate toward the end of the test (but actually improved in terms of feed conversion) indicates good stability of Catalyst C.

Reasonable variations, modifications and adaptations for various usages and conditions can be made within the scope of the disclosure and the appended claims, without departing from the scope of this invention.

That which is claimed:

1. A composition of matter consisting essentially of (a) at least one palladium-containing material selected from the group consisting of palladium metal and palladium oxide, (b) at least one silver-containing material selected from the group consisting of silver metal and silver oxide, (c) at least one alkali metal fluoride, and (d) at least one inorganic support material;

wherein the content of palladium in said composition is about 0.01–2 weight percent, the content of silver in said composition is about 0.02–10 weight percent, and the content of alkali metal in said composition is about 0.05–10 weight percent; and wherein said at least one inorganic support material is selected from the group consisting of alumina, silica, titania, zirconia, aluminosilicates, zinc aluminate, zinc titanate, and mixtures thereof.

2. A composition in accordance with claim 1, wherein said at least one alkali metal fluoride is potassium fluoride, and said at least one inorganic support material is alumina.

3. A composition in accordance with claim 1, wherein said content of palladium is about 0.05–0,6 weight percent, said content of silver is about 0.1–5 weight percent, and said content of alkali metal is about 0.2–5 weight percent.

4. A composition in accordance with claim 3, wherein said at least one inorganic support material is alumina, and said at least one alkali metal fluoride is potassium fluoride.

5. A composition in accordance with claim 4, wherein the atomic ratio of Ag to Pd is about 1:1 to about 20:1.

6. A composition in accordance with claim 5, wherein said atomic ratio is about 2:1 to about 10:1, and the surface area of said composition is about 1–200 $m^2/g$.

7. A composition in accordance with claim 1, having been prepared by a method which comprises contacting a starting material comprising palladium, silver and at least one inorganic support material with a solution comprising at least one alkali metal fluoride, drying the thus-contacted material, and calcining the thus-obtained dried material at a temperature of about 300°–600° C. for a time period of about 0.2–20 hours.

8. A composition in accordance with claim 7, wherein said at least one inorganic support material is alumina, said solution is aqueous, and said solution has a concentration of about 0.1–10 mol/l of said at least one alkali metal fluoride.

9. A composition in accordance with claim 8, wherein the weight ratio of said solution to said starting material is about 0.2:1 to about 2:1.

10. A composition in accordance with claim 8, wherein said at least one alkali metal fluoride is potassium fluoride.

11. A composition in accordance with claim 7, wherein said starting material has been treated with at least one dissolved reducing agent selected from the group consisting of formaldehyde, formic acid, ascorbic acid, dextrose, hydrazine and alkali metal borohydride at a temperature of up to about 60° C., before said contacting of said starting material with said solution comprising at least one alkali metal fluoride is carried out.

12. A composition in accordance with claim 11, wherein said at least one support material in said starting material is alumina, and said at least one alkali metal fluoride is potassium fluoride.

* * * * *